(12) United States Patent
Reape et al.

(10) Patent No.: US 7,556,150 B2
(45) Date of Patent: Jul. 7, 2009

(54) DISPENSER FOR PROGESTIN USED FOR ACUTE AND MAINTENANCE TREATMENT OF DUB

(75) Inventors: Kathy Reape, Bryn Mawr, PA (US); George Jones, Hillsdale, NJ (US)

(73) Assignee: Duramed Pharmaceuticals, Inc., Pomona, NY (US)

( * ) Notice: Subject to any disclaimer, the term of this patent is extended or adjusted under 35 U.S.C. 154(b) by 392 days.

(21) Appl. No.: 11/145,983

(22) Filed: Jun. 7, 2005

(65) Prior Publication Data
US 2005/0269238 A1   Dec. 8, 2005

Related U.S. Application Data

(60) Provisional application No. 60/577,217, filed on Jun. 7, 2004.

(51) Int. Cl.
*B65D 83/04* (2006.01)
(52) U.S. Cl. .................................. 206/534; 206/538
(58) Field of Classification Search ................ 206/438, 206/528, 529, 531, 532, 534, 534.1, 535, 206/538, 459.5
See application file for complete search history.

(56) References Cited

U.S. PATENT DOCUMENTS

| | | | |
|---|---|---|---|
| 3,414,119 A | 12/1968 | Finch, Jr. | |
| 3,942,641 A | 3/1976 | Segre | |
| 4,292,315 A | 9/1981 | Vorys | |
| 4,295,567 A | 10/1981 | Knudsen | |
| 4,512,986 A | 4/1985 | Reel et al. | |
| 4,736,849 A | 4/1988 | Leonard et al. | |
| D339,742 S | 9/1993 | Walchek, Jr. et al. | |
| 5,332,577 A | 7/1994 | Gertner et al. | |
| 5,368,187 A | 11/1994 | Poncetta et al. | |

(Continued)

FOREIGN PATENT DOCUMENTS

EP    0 852 208    7/1998

OTHER PUBLICATIONS

Bayer et al., "Clinical Manifestations and Treatment of Dysfunctional Uterine Bleeding," *JAMA*, vol. 269, No. 14, pp. 1823-1828 (Apr. 14, 1993).

(Continued)

*Primary Examiner*—Jacob K Ackun, Jr.
(74) *Attorney, Agent, or Firm*—Sterne, Kessler, Goldstein & Fox P.L.L.C.

(57) ABSTRACT

A dispenser including a first dispensing portion including one group of storage units for each of ten to twenty-eight days, and a second dispensing portion, including at least one storage unit for each of seventeen to thirty days. In the first dispensing portion, a first set includes a group of four storage units for each day, a second set includes a group of three storage units for each day, and a third set includes a group of two storage units for each day. The first dispensing portion contain a progestin. In the second dispensing portion, the first fourteen storage units contain a placebo and the remaining storage units contain a progestin. First and second dispensing portions may be provided as separate dispensing packs, or as a multi-pack of second dispensing portions. The dispenser is useful for treatment of acute episodes of dysfunctional uterine bleeding (DUB) and maintenance treatment for preventing future episodes of DUB.

22 Claims, 3 Drawing Sheets

U.S. PATENT DOCUMENTS

| | | | |
|---|---|---|---|
| 5,391,766 | A | 2/1995 | Klaus et al. |
| 5,747,480 | A | 5/1998 | Gast |
| 5,770,226 | A | 6/1998 | Hughes, Jr. et al. |
| 5,788,974 | A | 8/1998 | D'Amico et al. |
| 5,858,405 | A | 1/1999 | Gast |
| 5,888,543 | A | 3/1999 | Gast |
| 6,036,018 | A | 3/2000 | Harrold |
| D423,111 | S | 4/2000 | Davis et al. |
| 6,173,838 | B1 | 1/2001 | Brozell |
| 6,225,298 | B1 | 5/2001 | Spicer et al. |
| 6,338,408 | B1 | 1/2002 | Anderson |
| 6,375,956 | B1 | 4/2002 | Hermelin et al. |
| 6,451,780 | B1 | 9/2002 | Chwalsz et al. |
| 6,479,475 | B1 | 11/2002 | Gast |
| 6,564,945 | B1 | 5/2003 | Weinstein et al. |
| 6,583,145 | B1 | 6/2003 | Fensome et al. |
| 6,593,317 | B1 | 7/2003 | de Ziegler et al. |
| 6,602,521 | B1 | 8/2003 | Ting et al. |
| 6,610,674 | B1 | 8/2003 | Schreiber |
| 6,613,757 | B1 | 9/2003 | Garfield et al. |
| 6,667,050 | B1 | 12/2003 | Boissonneault et al. |
| 6,747,019 | B2 | 6/2004 | Casper et al. |
| 6,787,531 | B1 | 9/2004 | Hilman et al. |
| 2001/0016578 | A1 | 8/2001 | Spicer et al. |
| 2003/0004145 | A1 | 1/2003 | Leonard |
| 2003/0092602 | A1 | 5/2003 | Leach et al. |
| 2003/0181431 | A1 | 9/2003 | Hodgen |
| 2003/0191103 | A1 | 10/2003 | Grubb et al. |
| 2003/0207865 | A1 | 11/2003 | Dixon et al. |
| 2003/0216367 | A1 | 11/2003 | Pickar |
| 2003/0220377 | A1 | 11/2003 | Chesworth |
| 2003/0220494 | A1 | 11/2003 | Cameron et al. |
| 2003/0229057 | A1 | 12/2003 | Caubel et al. |
| 2003/0229072 | A1 | 12/2003 | Bullock et al. |
| 2003/0232753 | A1 | 12/2003 | Thorpe et al. |
| 2004/0002524 | A1 | 1/2004 | Chesworth et al. |
| 2004/0072808 | A1 | 4/2004 | Leonard |
| 2004/0176381 | A1* | 9/2004 | Walsh ........................ 514/251 |
| 2004/0180867 | A1 | 9/2004 | Casper et al. |
| 2004/0220152 | A1 | 11/2004 | Ben-Maimon et al. |
| 2004/0259851 | A1 | 12/2004 | Leonard |
| 2004/0266745 | A1 | 12/2004 | Schwanitz et al. |
| 2005/0051454 | A1* | 3/2005 | Coe et al. .................... 206/536 |
| 2005/0143359 | A1 | 6/2005 | Bell et al. |

OTHER PUBLICATIONS

Product Information Brochure from Parke-Davis/Warner Lambert Co. regarding its ESTROSTEP® product (1997).

Manzi et al, "Medical Management of Dysfunctional Uterine Bleeding," *The Endocrine Management of Benign Gynecologic Disease*, Chapman & Hall, Chapter 9, pp. 105-113 (1998).

Goldfarb, Alvin F, "Menstrual Dysfunction in the Adolescent Female," *The Endocrine Management of Benign Gynecologic Disease*, Chapman & Hall, Chapter 10, pp. 115-135 (1998).

Product Information Brochure from Novo Nordisk Pharmaceuticals, Inc. regarding its ACTIVELLA® product (2000).

Letter from the Department of Health and Human Services to Dr. Joseph S. Sonk of Wyeth-Ayerst Research regarding New Drug Application 18-405/S-016 filed Aug. 27, 1998, letter dated Apr. 12, 2000.

Webpage from website of Quest diagnostics, "Progestin for the treatment of dysfunctional uterine bleeding," listed a "last updated date" of Jan. 17, 2002. (actual date unknown).

Product Information Brochure from Ayerst Laboratories (A Wyeth-Ayerst Company) regarding ist AYGESTIN® product, dated Mar. 15, 2002.

Hickey et al., "Progestogens versus oestrogens and progestogens for irregular uterine bleeding associated with anovulation," *The Cochrane Library*, Issue 2 (2003) as republished by Update Software Ltd., pp. 1-10.

International Search Report and Written Opinion for International Application No. PCT/US2005/019803, mailed Oct. 7, 2005.

* cited by examiner

DISPENSER FOR PROGESTIN USED FOR ACUTE AND MAINTENANCE TREATMENT OF DUB

FIELD OF THE INVENTION

The present invention relates to a dispenser pack for the distribution of pharmaceuticals to be used in the treatment of acute dysfunctional uterine bleeding (DUB). The present invention is further related to a dispenser pack for the distribution of pharmaceuticals to be used in the maintenance or ongoing treatment of DUB for the prevention of future acute DUB. The present invention is further related to a dispenser for housing one or more dispenser packs of the present invention.

BACKGROUND OF THE INVENTION

Dysfunctional uterine bleeding (DUB) is excessive and prolonged or frequent bleeding that is not caused by pregnancy or disease. It may include abnormal or increased menstrual flow, or unexplained menorrhagia, which may include mild to severe clotting and last longer than 7 days. DUB may also be associated with unexplained anovulatory bleeding. Generally, DUB occurs in pubescent or peri-menopausal women, but may occur in women of any age. If left untreated, DUB may lead to iron deficiency, and eventually anemia.

The objectives for treating DUB include control of an acute bleeding episode and prevention of the reoccurrence of acute bleeding episodes. Several pharmaceuticals and pharmaceutical regimens are well-known for use in the treatment of DUB. For example, many women have been treated by the combination therapy of the administration of estrogen and progestin. Such combinations are often found in pharmaceuticals generally prescribed for oral contraception and hormone replacement therapy in menopausal women. DUB has also been treated with GnRH analogs, non-steroidal anti-inflammatory drugs or androgens. Surgical treatments, such as dilation and curettage (D&C) or hysterectomy have also been used in some cases to treat DUB, although surgical methods are very invasive and are typically avoided if treatment is possible through administration of pharmaceuticals.

Commercially available oral contraceptives that contain a combination of norethindrone acetate and ethinyl estradiol (combination estrogen and progestin product) have been used to treat DUB. However, the low daily dosages of estrogen and progestin in combination oral contraceptives, which limit the side effects caused by higher dosages while still providing effective contraception, are not sufficient for the treatment of an acute episode of DUB. Several treatment regimens for DUB utilizing combination oral contraceptive tablets have been described, but typically one to four combination oral contraceptive tablets must be taken per day for five to seven days to effectively stop the acute bleeding, followed by at least one twenty-eight-day pack of oral contraceptive tablets with one tablet administered daily. Further, research shows that the use of progestins alone, such as norethindrone acetate or medroxyprogesterone acetate, to treat DUB is associated with less nausea and vomiting and may be associated with a lower risk to patients of venous thromboembolism than either high dose estrogen given alone or in combination with a progestin.

For example, it is known to treat DUB by administering a daily dosage of either norethindrone acetate or medroxyprogesterone acetate, where the daily dosage is the same on some days and different on others. When multiple doses are taken on the same day, patients are generally encouraged to space the dosages throughout the day. As a result, patients need to keep track of which day of the regimen it is, how many pills to take that day and when to take them. Further complicating this treatment is that the prescribed oral dosages of norethindrone acetate and medroxyprogesterone acetate are in an amount greater than that usually provided in oral contraceptives (such as 5 mg tablets of norethindrone acetate or 10 mg tablets of medroxyprogesterone acetate). Consequently, they are presently only dispensed to patients in bulk, meaning multiple pills in a single bottle. Generally, the pill bottle will be supplied by the pharmacist with the instructions for the prescribed dosage on the bottle and with enough tablets included to last for the entire duration of the regimen. Because the tablets are dispensed in bulk, it is difficult for patients to properly comply with the complex dosage regimen prescribed for DUB. Lack of proper compliance can cause recurrence of the DUB symptoms and may lead to more invasive treatment such as surgery. Also, lack of compliance among patients limits a physician's ability to determine the effectiveness of the regimen prescribed for an individual patient or for research purposes. Further, a single pill bottle full of pills makes it difficult for a patient to remember if a particular dosage has already been taken on a particular day, thus creating a high probability of improper dosing. Hence, the need exists for a simple, yet effective means of simply and accurately dispensing a regimen for the treatment of DUB which has the likelihood of increasing patient compliance.

BRIEF SUMMARY OF THE INVENTION

The present invention is directed to a dispenser pack for dispensing pharmaceuticals for the treatment of acute episodes of DUB and/or for the prevention of further acute episodes of DUB through maintenance treatment.

One aspect of the present invention includes a dispenser having a first dispensing portion for dispensing an oral dosage of a pharmaceutical, such as for the treatment of an acute episode of DUB. The first dispensing portion includes a plurality of storage units for enclosing the oral dosage form of a pharmaceutical, including one group of storage units for each of a pre-determined number of consecutive days. The dispenser also includes at least one second dispensing portion. The second dispensing portion includes at least one storage unit for a pre-determined number of consecutive days. For example, the first dispensing portion may be a blister pack in which the blisters are labeled for each day the oral dosage inside is to be taken. By providing a group of storage units associated with each day of the regimen, patients are provided a convenient tool to aid in compliance with a complex prescription. In particular, the first and second dispensing portions instruct the patient as to when a dosage is to be taken to avoid missed dosages and reminds the patient of already taken dosages to avoid accidental overdosing. The dispenser of the present invention is well suited for use with a progestin for the treatment of DUB, such as norethindrone acetate or medroxyprogesterone acetate. A dispensing portion of the dispenser may be a blister pack or a blister card such that each storage unit therein is a blister. Each dispenser may contain several second dispensing portions, which may be displayed on one or more of a blister type card, such that the patient has several months' worth of treatment by filling a single prescription.

Another aspect of the present invention is a dispenser for an oral dosage form of a pharmaceutical comprising a first dispensing portion including ten to twenty-eight groups of storage units wherein one group is provided per day. The dispenser further comprises a second dispensing portion including seventeen to thirty storage units wherein one unit is provided per day. An oral dosage form of a progestin is contained in each of the storage units of the first dispensing portion.

Yet another aspect of the present invention is a dispenser pack for an oral dosage form of a pharmaceutical including the first dispensing portion of the dispenser for the treatment of acute episodes of DUB. The dispenser pack includes a first set of storage units for an initial daily dosage of a progestin, and at least a second set of storage units for a second daily dosage of a progestin, wherein the daily dosage in the second set is less than the daily dosage in the first set; and wherein the daily dosage in any successive set is less than the daily dosage of the set preceding it; and wherein each set of storage units is arranged consecutively following the first set of storage units.

Yet another aspect of the present invention is a dispenser pack for an oral dosage form of a pharmaceutical including the second dispensing portion of the dispenser for the maintenance treatment of DUB. The dispenser pack includes a first set of storage units and a second set of storage units, where the second set of storage units are arranged consecutively to follow the first set of storage units. Each of the first set of storage units contains an oral dosage of either a placebo or a health supplement. Meanwhile, each of the second set of storage units contains an oral dosage of a progestin, such as norethindrone acetate or medroxyprogesterone acetate.

The dispenser pack for an oral dosage form of a pharmaceutical may further comprise a first group of storage units for an initial daily dosage of a pharmaceutical and a second group of storage units for a second daily dosage of the pharmaceutical, wherein the daily dosage in the second group is less than the daily dosage in the first group and wherein the second group of storage units is arranged consecutively following the first group of storage units.

Each dispenser pack of the present invention may include day indicators for each day of the regimen, and each storage unit may include a time-of-day indicator. Also the dispenser pack may be a blister pack or a blister card such that each storage unit therein is a blister.

It is apparent from the above description that known regimens for the treatment of acute and chronic DUB episodes are often complex and require a precise adherence to the regimen for maximum effectiveness. Thus, the dispenser and/or a dispenser pack of the present invention are convenient and simple to use and aid in compliance of the prescribed regimen.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

BRIEF DESCRIPTION OF THE DRAWINGS/FIGURES

The accompanying drawings, which are incorporated herein and form a part of the specification, illustrate the present invention and, together with the written description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION OF THE INVENTION

Most of the recommended regimens for the treatment of acute DUB are tapered so that a first daily dosage of the pharmaceutical, such as a progestin, is taken for one or more days and then the daily dosage is lowered for a certain number of days after that. The dosage can also be lowered a second time for a certain number of days following that course. These tapered dosage regimens are often complex, and may last from ten to twenty-eight days. Progestins may be dispensed as tablets or another dosage form which would be apparent to one skilled in the art, for example as capsules, gel capsules, orally disintegrating or rapidly disintegrating tablets and effervescent tablets. Since several dosages are to be taken per day, it is preferred that dosages are spread out throughout the day. However, a single extended release pharmaceutical that includes the total daily dosage of the progestin may be used instead.

One regimen for the treatment of an acute episode of DUB is the administration of four doses of from 2.5 to 10 mg of norethindrone acetate, and preferably 5 mg, for a daily total of 20 mg, in spaced out intervals on a first day of treatment, followed by three doses of norethindrone acetate, and preferably 5 mg each, for a daily total of 15 mg, in spaced out intervals for the next three days, followed by two doses of norethindrone acetate, and preferably 5 mg each, for a daily total of 10 mg, in spaced out intervals for the next ten days. An alternative regimen may replace norethindrone acetate with an equally effective amount of another progestin, such as medroxyprogesterone acetate, norethindrone or micronized progesterone.

Figure 1:
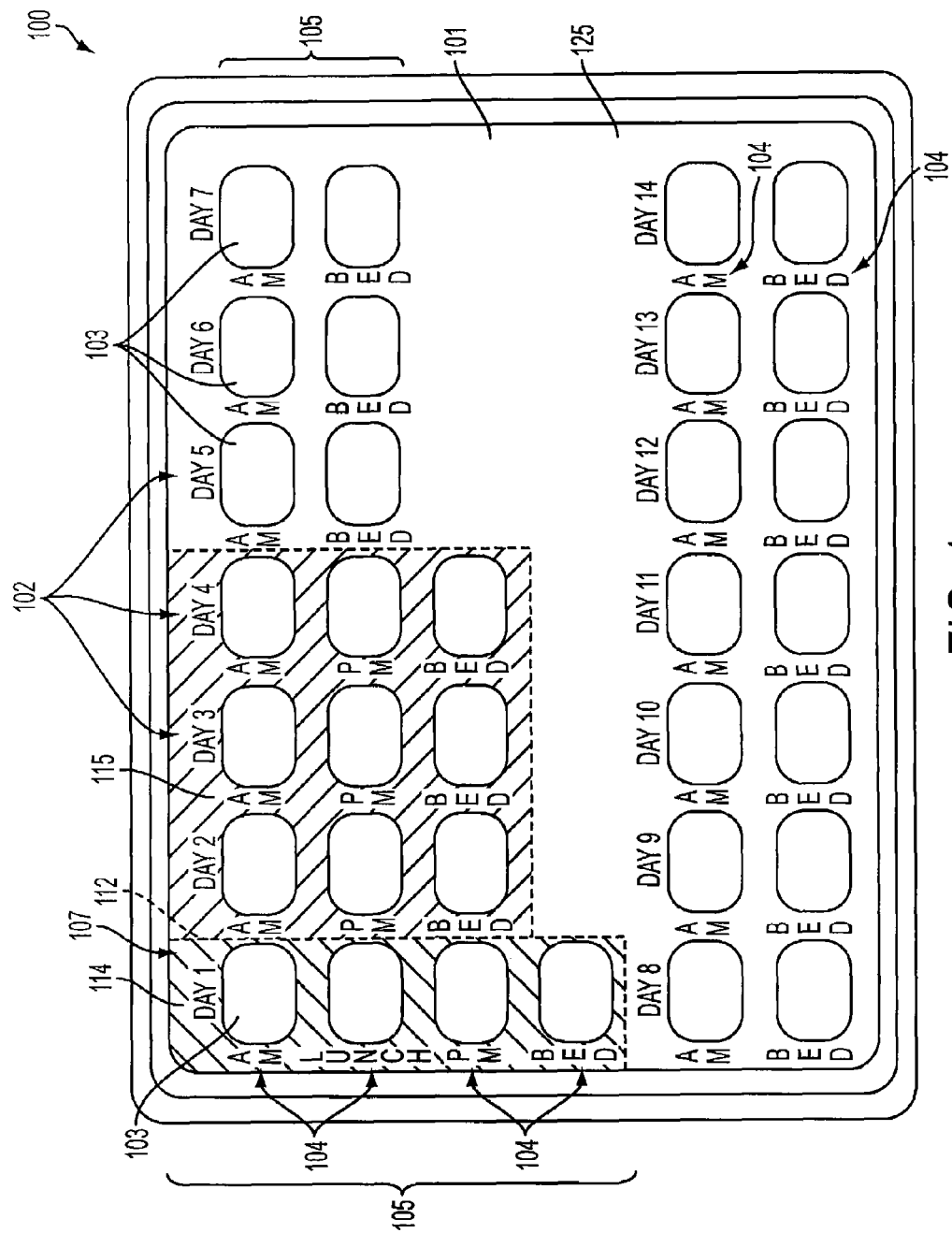
FIG. 1 is a first dispenser pack of the present invention enclosing a preferred regimen for the treatment of acute episodes of DUB.

FIG. 1 shows an example of a dispenser pack 100 of the present invention for use with the preferred regimen discussed above for use in the treatment of an acute episode of DUB. In the example of FIG. 1, dispensing pack 100 is a conventional blister pack, such as those generally used for holding various prescription and over-the-counter pharmaceuticals. Generally, a blister pack may be formed from a sheet 101 of a thin polymeric or thermoplastic material molded to have individual storage units or blisters formed therein, such as the blisters 103 shown in FIG. 1. An oral dosage form of a pharmaceutical is then placed within each blister 103, which are then covered to contain the pharmaceutical. Typically, a foil or other covering that is cleavable with a minimum amount of applied pressure is used to cover the blisters 103. To remove the pharmaceutical, the user applies pressure to the blister 103 causing the pharmaceutical to press against the covering and the covering to rupture, so that the pharmaceutical is accessible to the user. Dispenser packs, other than the blister type described herein may be used with the present invention provided that the dispenser pack separately stores and provides access to the prescribed dosages.

Dispensing pack 100 includes fourteen groups 105 of storage units 103. Each group 105, in FIG. 1, is for a single day of the preferred regimen discussed above. As such, day indicators 102 printed directly on sheet 101 or, for example, on an insert viewable through the plastic material of sheet 101, are numbered consecutively on pack 100 to show each day of the regimen. While fourteen day indicators 102 are shown in FIG. 1, an acute regimen may have between ten and twenty-eight total days. As such, dispensing pack 100 may have more or fewer groups 105 of storage units 103 to correspond to the total days of the particular regimen being used.

In FIG. 1, groups 105 of dispensing pack 100 are arranged into three sets, wherein each group 105 in the same set dispenses the same daily dosage of progestin. The first set 114 consists of one group 105 that includes a first daily dosage of progestin enclosed in four storage units 103, which are aligned under a "Day 1" indicator 107. The second set 115 consists of three groups 105 associated with the next three day indicators 102, labeled "Day 2," "Day 3," and "Day 4," respectively. Each group 105 in second set 115 includes a second daily dosage of a progestin enclosed in three storage units 103. The third set 125 consists of ten groups 105 of storage units 103 associated with the remaining day indicators 102, labeled "Day 5" to "Day 14", respectively. Each group 105 of third set 125 includes a third daily dosage of progestin enclosed in two storage units 103. Other wording, numbering or indicia could be used to identify the particular group 105 of storage units 103 that are to be associated with a particular day of the regimen.

Each storage unit 103 may also have a time-of-day indicator 104 positioned adjacent thereto to indicate at what time of day the dosage within the storage unit 103 should be taken. For example, in FIG. 1, the four storage units 103 of the first group 105 are, in order, labeled with time-of-day indicators 104 reading "AM," "lunch," "PM," and "Bed" to indicate that they are to be associated with a dosage to be taken in the morning, at lunchtime, in the afternoon, and at bedtime respectively. It would also be apparent to one skilled in the art that other words, numbers, logos or indicia may be used to symbolize various times of day. Also, other time intervals or no time intervals may be used with the dispenser pack of the present invention.

Each storage unit 103 of the dispensing pack 100 includes a single dosage of a progestin (not shown). Preferably, each storage unit 103 includes between 2.5 and 10 mg and preferably 5 mg of norethindrone acetate or an equivalent effective amount of norethindrone acetate or of another progestin, such as medroxyprogesterone acetate. Dispensing pack 100 of FIG. 1 can be used for a variety of different regimens by varying the amount of progestin enclosed in each storage unit 103, by varying the number of storage units 103 in each group 105, or by including more than one dosage in each storage unit 103.

Example regimens for the treatment of acute episodes of DUB are listed in Table 1 below.

TABLE 1

| Schedule | Progestin |
| --- | --- |
| Three doses per day for three days and<br>Two doses per day for eleven days | 5 mg of norethindrone acetate or 10 mg of medroxyprogesterone acetate |
| Four doses per day for four days;<br>Three doses per day for three days; and<br>Two doses per day for seven days | 5 mg of norethindrone acetate or 10 mg of medroxyprogesterone acetate |
| One dose every 4 hours for 24-48 hours;<br>Four doses per day for four days; | 5 mg of norethindrone acetate or 10 mg of |

TABLE 1-continued

| Schedule | Progestin |
| --- | --- |
| Three doses per day for three days; and<br>Two doses per day for two weeks | medroxyprogesterone acetate |

The embodiment disclosed in FIG. 1 may be adjusted to suit any of these regimens or any other regimen for the treatment of DUB by altering the number of storage units 103.

Dispensing pack 100 may be modified in a number of ways and still clearly assist in aiding the patient in compliance with the prescribed regimen. For example, groups 105 and day indicators 102 may be arranged in a format other than consecutively numbered rows. For example, day indicators 102 may be arranged in a circle, square or other arrangement. Further, storage units 103 may be grouped in a format other than a line, such as a circle, a cluster, or other arrangement provided that it is clear which storage units 103 correspond with which day indicators 102.

Alternatively, time-of-day indicators 104 may be located nearby a group 105 of storage units 103 as a reminder of the dosage spacing or the patient may manually mark off some form of time-of-day indicator once the dosage in a storage unit 103 has been taken. This permits the patient to easily determine how many dosages have been taken that day and how many are remaining. The various sets of dispensing pack 100 may also be segmented by color coding 112, for example, or other means of visible separation to distinguish between each day or set of days of the regimen.

We turn now to a maintenance treatment to prevent future acute episodes of DUB, which includes administering a pharmaceutical, such as progestin, at a fixed daily dose for five to fourteen days beginning twelve to sixteen days after the first day of a patient's menstrual period. In the preferred regimen, the progestin is administered on day 15, with day 1 being the first day of menstrual bleeding, and continues for ten days.

In the preferred regimen one dose of 2.5 to 10 mg, and preferably 5 mg of norethindrone acetate, is to be taken each day for ten days. In the alternative, an equally effective amount of norethindrone acetate or of another progestin, such as medroxyprogesterone acetate or norethindrone, may be used. Also in the preferred embodiment, a placebo or a health supplement, such as an iron supplement, a folic acid supplement, a calcium supplement, or another health supplement, may be administered in a daily dose prior to the first dose of progestin for a total regimen of seventeen to thirty days. This helps with patient compliance because the patient takes a dose of something every day.

Figure 2:
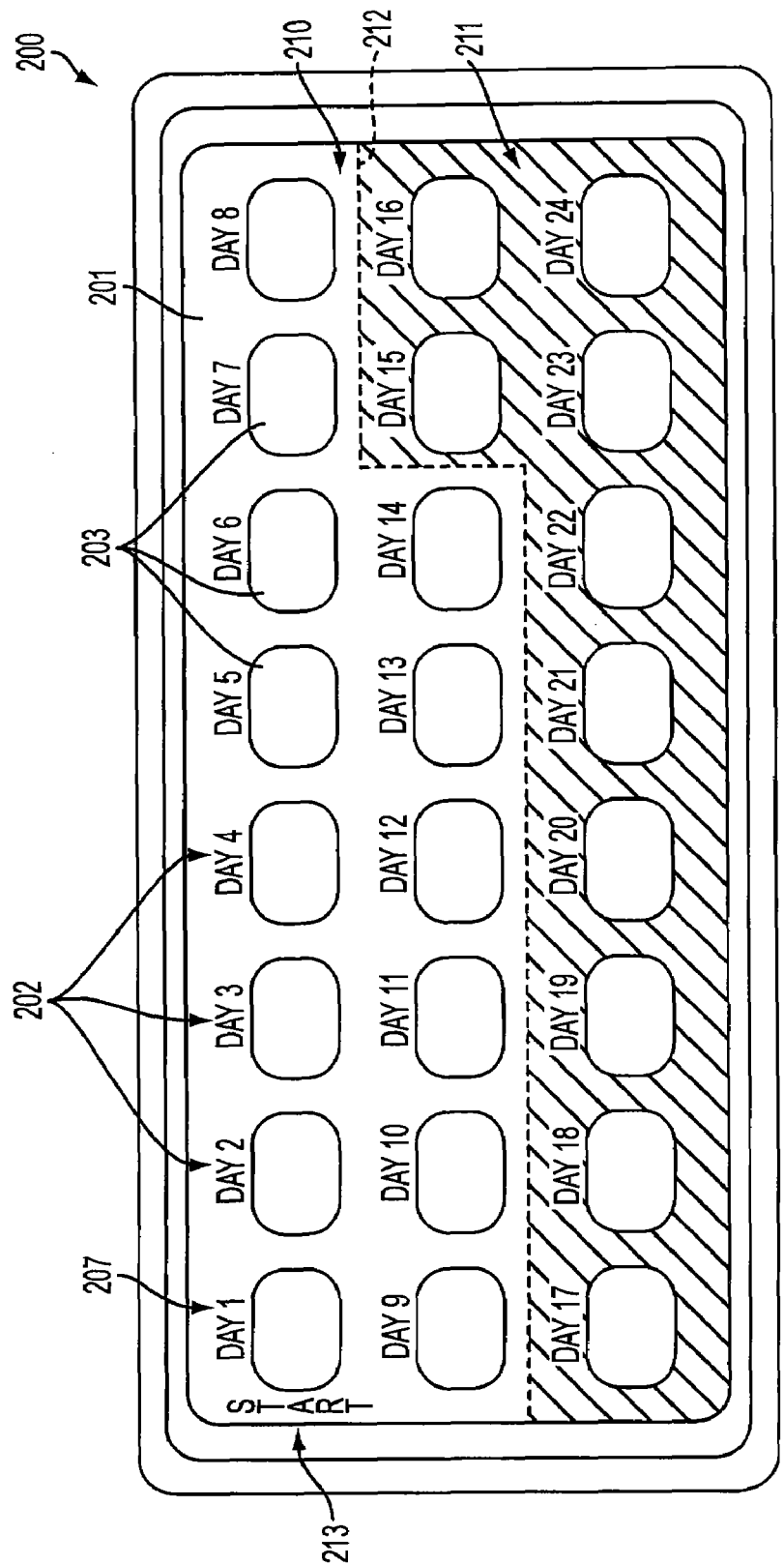
FIG. 2 is a second dispenser pack of the present invention enclosing a preferred regimen for the maintenance treatment of DUB.

FIG. 2 shows a preferred dispensing pack 200 specifically designed to be used with the preferred maintenance treatment regimen discussed above. Similar to dispensing pack 100 of FIG. 1 above, dispensing pack 200 is a conventional blister pack, such as those generally used for holding various prescription and over-the-counter pharmaceuticals. Further, dispensing pack 200 is made from a molded sheet 201 of foil, plastic or other material and is manufactured and functions similarly to that described above for dispensing pack 100.

Dispensing pack 200 includes a plurality of storage units 203. Each storage unit 203 is for a single day of the preferred regimen discussed above. As such, day indicators 202 printed directly on sheet 201, or for example on an insert viewable through sheet 101, are numbered consecutively to show each day of the regimen. Each day indicator 202 has a single storage unit 203, in this case a blister, corresponding thereto.

However, as mentioned above, a maintenance regimen may have as many as thirty days. As such, dispensing pack 200 may have more or fewer storage units 203 to correspond to the total number of days of the regimen being used.

In FIG. 2, a first day indicator 207 is labeled "Day 1." First day indicator 207 may also include a written instruction 213 identifying that the first day indicator 207 is also associated with the first day of the patient's menstrual cycle. A first set 210 of storage units 203 are associated with day indicators 202 labeled "Day 1" to "Day 14." Other labels, words, numbers, logos or indicia could be used to identify each day.

Each storage unit 203 of the first set 210 of storage units includes an oral dosage form (not shown) of a placebo or a health supplement, such as an iron supplement, a folic acid supplement, a calcium supplement, or another health supplement apparent to one skilled in the art. As an alternative, the first set 210 of storage units 203 may be empty. However, if empty, it is preferred that the patient has some way to indicate the passing of each day, for example, by rupturing an empty storage unit 203 as if there were a dosage therein. Alternatively, dispensing pack 200 may have no blisters at all for the first fourteen days and instead may have a way to manually indicate the passing of each day leading up to the time for taking the active medication.

A second set 211 of storage units 203, as shown associated with day indicators labeled "Day 15" to "Day 24," each encloses a progestin dosage (not shown). Preferably, each storage unit 203 includes either 5 mg of norethindrone acetate or an equivalent effective amount of norethindrone acetate or of another progestin, such as medroxyprogesterone acetate. The amount of each progestin may be modified in various regimens. Dispensing pack 200 of FIG. 2 can be used for a variety of different regimens by varying the amount of progestin in each storage unit 203, by enclosing more than one dosage in each storage unit 203 or by increasing or decreasing the number of storage units 203.

Dispensing pack 200 may be modified in a number of ways and still clearly assist in aiding the patient in compliance with the prescribed regimen.

For example, storage units 203 and day indicators 202 may be arranged in a format other than consecutively numbered rows. For example, they may be arranged in a circle, square or other arrangement provided that it is clear which storage unit is associated with which day indicator 202.

Second set 211 of storage units 203 may further include an additional storage unit (not shown) for each day. This additional storage unit may include a health supplement, such as an iron supplement, a folic acid supplement, a calcium supplement, or another supplement that would be apparent to one skilled in the art. Additional storage units may be added to the regimen either in lieu of or in addition to the use of any health supplements in the first set 210 of storage units 203. Dispensing pack 200 may also have additional storage units 203 and additional day indicators 202 associated therewith enclosing such health supplements added at the end of the preferred regimen for each of an additional 2-10 days, most preferably for a total of 28 days in the maintenance regimen dispensing pack, which is the average number of days of a menstrual cycle.

Alternatively, there may be more than one storage unit 203 for each day. If this is the case, each storage unit 203 may be labeled with a time-of-day indicator, similar to those shown in FIG. 1, or having other words, numbers, logos, or indicia to symbolize dosage time. Storage units 203 may be grouped with respect to their associated day indicator 202 in a line, a circle, a cluster, or other arrangement.

Sets 210 and 211 of dispensing pack 200 may be divided by color coding or other means of visible separation 212 to distinguish between them and to inform the patient as to which are the placebo or health supplement dosages and which are the active dosages. The active dosages may also be distinguished from the placebo or health supplement dosage by being a different color.

Figure 3:
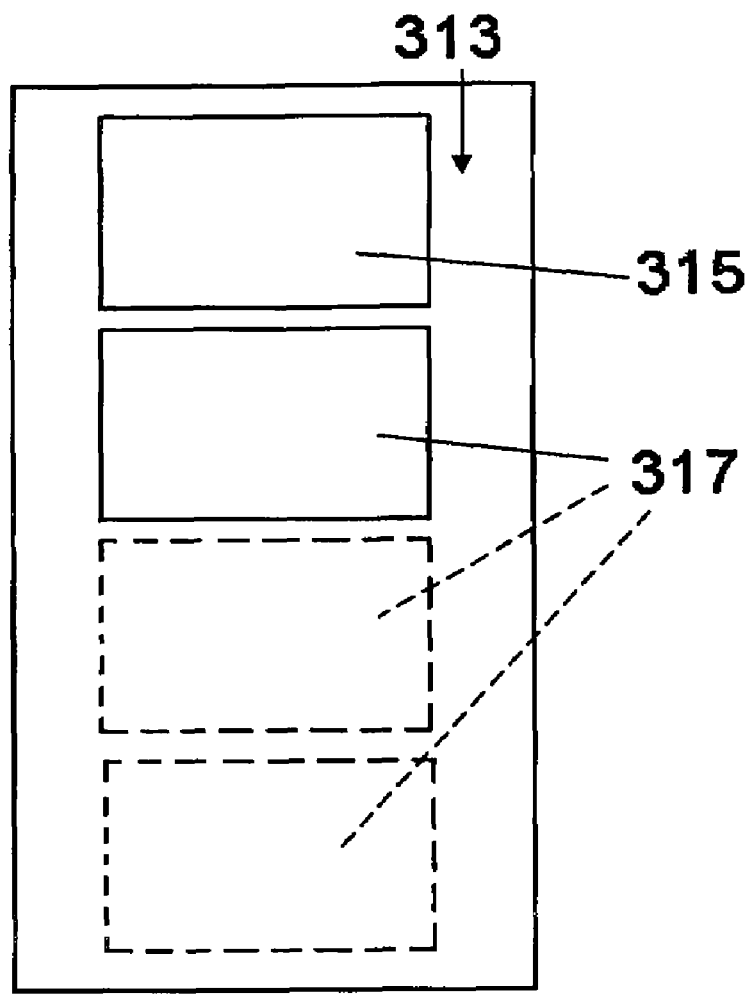
FIG. 3 is a dispenser of the present invention enclosing a first dispenser pack and several second dispensing packs of the present invention for the treatment of acute episodes of DUB and the maintenance treatment of DUB.

In a preferred treatment regimen, an acute treatment is followed with maintenance treatments for up to three menstrual cycles thereafter. A patient would be first treated with an acute dispensing pack 100, such as that shown in FIG. 1, followed by at least one maintenance dispensing pack 200, such as that shown in FIG. 2. As shown schematically in FIG. 3, a dispenser 313 may be provided which encloses a first dispensing portion 315 and at least one, and preferably three, second dispensing portions 317. First dispensing portion 315 is designed for the treatment of an acute episode of DUB and may be first dispenser pack 100 of FIG. 1 or a different dispensing pack according to the present invention. Each second dispensing portion 317 is designed for the maintenance treatment of DUB and may be a second dispenser pack 200 of FIG. 2 or a different dispensing pack according to the present invention. Further as shown in phantom in FIG. 3, more than one second dispensing portion may be included in a dispenser 313. One advantage of a dispenser 313 including both an acute regimen and a maintenance regimen is that a patient does not need to have their prescription filled for several months. Alternatively, dispenser 313 may contain no acute regimen treatment, i.e. no first dispensing portion, and may contain only one or more maintenance regimen treatments, i.e. only second dispenser portions according to the present invention.

While the present invention has been particularly shown and described with reference to preferred embodiments thereof, it will be understood by those skilled in the art that they have been presented by way of example only, and not limitation, and various changes in form and details can be made therein without departing from the spirit and scope of the invention.

Thus, the breadth and scope of the present invention should not be limited by any of the above-described exemplary embodiments, but should be defined only in accordance with the following claims and their equivalents.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A dispenser for an oral dosage form of a pharmaceutical, comprising:

a first dispenser pack corresponding to a treatment regimen, including a plurality of storage units, including a group of storage units for each day of the treatment regimen, wherein each storage unit includes the same dosage of a pharmaceutical, and wherein each group of storage units is labeled with an indicator so as to identify when the pharmaceutical should be administered, wherein said indicators are such that the number of storage units identified for a first treatment day is greater than the number of storage units identified for a second treatment day, the number of storage units identified for each of a third and fourth treatment day is the same as the number of storage units identified for said second treatment day, the number of storage units identified for said fourth treatment day is greater than the number of storage units identified for a fifth treatment day, and the number of storage units identified for each day of a sixth through fourteenth treatment day is equal to the number of storage units identified for said fifth treatment day;

at least one second dispenser pack corresponding to a maintenance treatment regimen, including a plurality of storage units, including a single storage unit for each day of said maintenance treatment regimen, wherein for each day of a first through fourteenth treatment day, a placebo or health supplement is included in said storage unit, and wherein, for each day of a fifteenth through twenty-fourth treatment day, a dosage of a pharmaceutical is included in the storage unit, said dosage of said pharmaceutical being the same on each of said fifteenth through twenty-fourth treatment days.

2. The dispenser as set forth in claim 1, wherein at least some of said storage units are blisters.

3. The dispenser as set forth in claim 1, wherein said first dispenser pack includes a total of fourteen treatment days.

4. The dispenser as set forth in claim 3, wherein said indicators are such that four storage units are identified for said first treatment day of said first dispenser pack.

5. The dispenser as set forth in claim 4, wherein said indicators are such that three storage units are identified for each of said second, third, and fourth treatment days of said first dispenser pack.

6. The dispenser as set forth in claim 5, wherein said indicators are such that two storage units are identified for each of said fifth through fourteenth treatment days of said first dispenser pack.

7. The dispenser as set forth in claim 6, wherein each storage unit in said first dispenser pack contains an oral dosage form of a progestin.

8. The dispenser as set forth in claim 7, wherein said oral dosage form of a progestin is norethindrone acetate or medroxyprogesterone acetate.

9. The dispenser as set forth in claim 8, wherein said oral dosage form of a progestin is 5 mg of norethindrone acetate or 10 mg of medroxyprogesterone acetate.

10. The dispenser as set forth in claim 1, wherein said health supplement is iron, folic acid or calcium.

11. The dispenser as set forth in claim 1, wherein an oral dosage form of a progestin is included in the storage unit for each of said fifteenth through twenty-fourth treatment days of each said second dispenser pack.

12. The dispenser as set forth in claim 1, wherein each said second dispenser pack includes a total of twenty-four storage units.

13. The dispenser as set forth in claim 11, wherein said oral dosage form of a progestin is norethindrone acetate or medroxyprogesterone acetate.

14. The dispenser as set forth in claim 13, wherein said oral dosage form of a progestin is 5 mg of norethindrone acetate or 10 mg of medroxyprogesterone acetate.

15. The dispenser as set forth in claim 1, wherein each storage unit in said first dispenser pack contains one of 20 mg of norethindrone acetate or 40 mg of medroxyprogesterone acetate.

16. The dispenser as set forth in claim 1, wherein each storage unit in said first dispenser pack contains one of 15 mg of norethindrone acetate or 30 mg of medroxyprogesterone acetate.

17. The dispenser as set forth in claim 1, wherein each storage unit in said first dispenser pack contains one of 10 mg of norethindrone acetate or 20 mg of medroxyprogesterone acetate.

18. The dispenser as set forth in claim 1, wherein at least one of said indicators for at least one group of storage units includes an indicium for each storage unit in the group.

19. The dispenser as set forth in claim 18, wherein the indicium for each storage unit is a time-of-day indicator.

20. The dispenser as set forth in claim 1, wherein said dispenser includes at least two second dispenser packs.

21. The dispenser as set forth in claim 1, wherein at least one of said first dispenser pack and said second dispenser pack is a blister pack.

22. The dispenser as set forth in claim 1, wherein said first dispenser pack and said second dispenser pack are separate blister packs.

* * * * *